Figure 1:
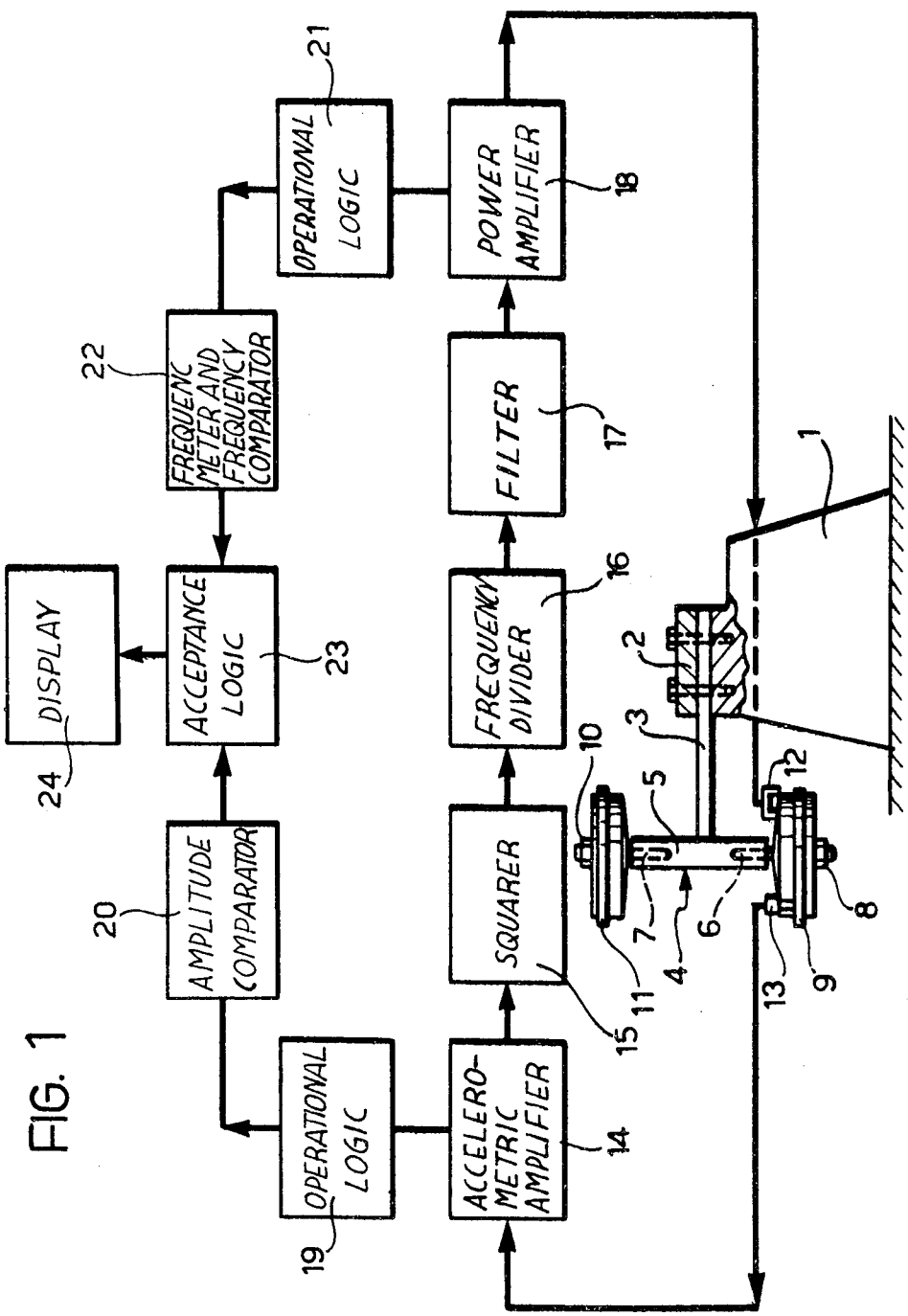

United States Patent [19]  [11]  4,122,723
Levizzari et al.  [45]  Oct. 31, 1978

[54] METHOD AND APPARATUS FOR TESTING THE QUALITY OF CAST IRON PIECES ESPECIALLY SPHEROIDAL CAST-IRON PIECES

[75] Inventors: Giannetto Levizzari; Giacomo Ruspa, both of Turin, Italy

[73] Assignee: Fiat Societa per Azioni, Turin, Italy

[21] Appl. No.: 741,072

[22] Filed: Nov. 11, 1976

[30] Foreign Application Priority Data

Nov. 25, 1975 [IT] Italy .................. 69903 A/75

[51] Int. Cl.² ........................ G01H 13/00
[52] U.S. Cl. ................................ 73/579
[58] Field of Search ............... 73/67.2, 67.3, 67.4

[56] References Cited
U.S. PATENT DOCUMENTS 3,043,132 7/1962 Schubring ................... 73/67.2
3,284,192 11/1966 Larson et al. ............. 73/67.2 X
3,481,185 12/1969 Ittner ........................ 73/67.2

FOREIGN PATENT DOCUMENTS 2,534,953 2/1976 Fed. Rep. of Germany ........... 73/67.2
1,226,901 3/1971 United Kingdom ................. 73/67.2

Primary Examiner—Richard C. Queisser
Assistant Examiner—John P. Beauchamp
Attorney, Agent, or Firm—Sughrue, Rothwell, Mion, Zinn and Macpeak

[57] ABSTRACT

Spheroidal cast iron pieces are tested by clamping each individual piece on a vibratory test rig together with a reference datum piece and using the measured amplitude and frequency of the system at resonance to derive an automatic indication, through an electronic logic circuit, of the quality of the piece under test compared with the reference piece.

5 Claims, 2 Drawing Figures

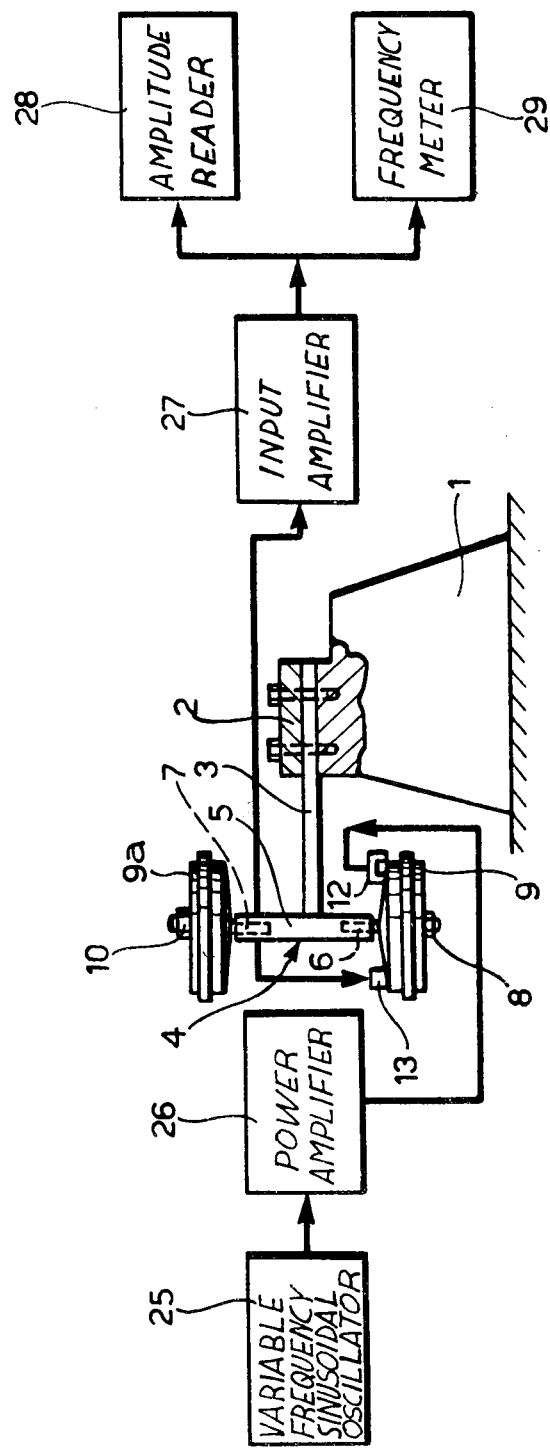

METHOD AND APPARATUS FOR TESTING THE QUALITY OF CAST IRON PIECES ESPECIALLY SPHEROIDAL CAST-IRON PIECES

This invention relates to a method of and apparatus for testing the quality of cast iron pieces, particularly pieces of spheroidal cast iron.

As is known, the spheroidization treatment of cast iron pieces, while being advantageous from the point of view of mechanical results, can result in incomplete spheroidization of the graphite in the cast iron pieces. It is therefore necessary to carry out a 100% check of the quality of spheroidal cast iron pieces made on a production line.

Conventional methods of testing cast iron pieces are based on ultrasonic methods. Thus two known ultrasonic methods of testing are based upon (a) the attenuation of an ultrasonic signal, and (b) the speed of propagation of an ultrasonic signal through a test piece.

The first method (a) is based upon the fact that the coefficient of attenuation of an ultrasonic wave is lower in completely spheroidized cast iron than in cast iron which is partially spheroidized or cast iron which has casting defects; by measurement of a bottom echo of an ultrasonic signal after transmission through a casting it is possible to evaluate the quality of the casting. It is, however, difficult to obtain good ultrasonic connections between an ultrasonic transducer and a cast iron piece being tested when the latter has not undergone a surface finishing operation and therefore has a rough, uneven surface. This in turn may prevent accurate measurement of the bottom echo.

The second method (b) is based upon the fact that the speed of propagation of an ultrasonic signal in a casting is greater in a perfectly spheroidized casting than in a casting which is partially spheroidized or not spheroidized at all, or which has casting anomalies. This method, too, has practical disadvantages in that the accurate determination of the length of a propagation path of an ultrasonic wave in the piece being tested is both tedious and difficult.

An object of the invention is to provide a method, applicable to large batch production, for rapid checking of the degree of spheroidization of spheroidal cast iron pieces, particularly pieces having a complex geometry, such as, for example, crank shafts or brake drums, avoiding the above-mentioned disadvantages.

The present invention provides a method for testing the quality of cast iron pieces, which is characterised by oscillating at resonance a system formed by a piece to be tested and a reference or datum piece having the same form and geometry as the piece to be tested, mechanically coupled together, measuring the frequency and resonance amplitude of the system and using said measurements to evaluate the quality of the piece to be tested.

The invention also provides an apparatus for carrying out the aforesaid method of testing, characterised in that it comprises:

a fixed support structure;

a support extending cantilever fashion from the said support structure;

first fixing means for fixing a reference or datum piece to the said support;

second fixing means for fixing a piece to be tested to the said support;

a transducer adapted to be attached to the said reference or datum piece in use of the apparatus in order to excite vibration of the mechanical system consisting of the support, the reference or datum piece and the piece under test after the latter have been affixed to the support;

accelerometer means adapted to be applied to the said reference or datum piece for measuring the vibrations of the said mechanical system, and an electronic circuit connected to the said transducer and to the said accelerometer means for effecting resonant oscillations of the said mechanical system, measuring the amplitude and frequency of said oscillations, comparing the said measurements with pre-established threshold values and providing an indication of the result of such comparison.

The present invention has the advantage of enabling rapid testing of cast iron pieces to be carried out without the difficulties associated with ultrasonic testing methods of the kind referred to earlier.

The invention will be further described, by way of non-limiting example, with reference to the accompanying diagrammatic drawings, in which:

FIG. 1 is a block schematic diagram illustrating one embodiment of an apparatus for carrying out a method of testing according to the present invention, and FIG. 2 is a block schematic diagram illustrating a circuit for calibration of an apparatus according to the invention.

Referring to FIG. 1 there is shown a fixed support structure 1 to which there is affixed, by means of a clamp 2, the free end of a stem 3 of a metal T shaped support or mounting element 4. As illustrated in the drawings, the stem 3 extends horizontally in cantilever fashion from the support 1 and has a cross-piece 5 which extends vertically. Threaded pins 6 and 7 are screwed into the ends of the cross-piece 5.

To the lower end of the cross-piece 5 there is affixed, by means of a nut 8 screwed on to the threaded pin 6, a reference piece 9 made by casting in spheroidal cast iron and constituting a datum piece. In the example illustrated the reference piece 9 consists of a brake drum for a motor vehicle wheel. To the upper end of the cross-piece 5 there is affixed, by means of a nut 10 screwed on to the threaded pin 7, a piece 11, the quality of which is to be tested. The piece 11 has the same form and geometry as the reference piece and is actually substituted for reference piece 9a following initial calibration as explained hereafter in regard to FIG. 2.

For the purpose of testing of large series of pieces from a production line means could be provided, for example pneumatically controlled means, for rapid locking and release of individual pieces 11 to be tested in relation to the upper end of the cross-piece 5, whilst the reference piece 9 remains fixed to the lower end of the cross-piece 5 during the testing of an entire batch of pieces 11.

A transducer 12 is fixed to the reference piece 9 and is arranged to cause vibration of the mechanical system consisting of the mounting element 4, the reference piece 9, and the piece 11 being tested. Also affixed to the reference piece 9 is an accelerometer 13 for registering the vibrations of the said mechanical system.

The accelerometer 13 and the transducer 12 are connected in an electronic circuit comprising an amplifier 14 which receives the signals (bottom vibrations) from the accelerometer 13 and passes the amplified signals to a squarer 15 the output of which is fed to a frequency divider 16. The output of the frequency divider 16 is passed to the input of a filter 17 which passes only the components of the square wave at or close to the resonance frequency of the vibratory mechanical system. These resonant frequency components at the output of the filter 17 are amplified in a power amplifier 18 the output of which drives the transducer 12. The transducer 12 will therefore excite the mechanical system consisting of the T shaped mounting element 4, the reference piece 9, and the piece 11 under test through the feedback loop described above until a stable condition of excitation of the system at the resonance frequency is reached.

Once the stable condition of resonant excitation has been established, the amplitude and frequency of the resonant oscillations are compared with pre-established threshold values, in order to verify whether the piece 11 under test is acceptable or whether it has to be rejected. For this purpose the output signal from the accelerometer 13, amplified by the amplifier 14 is fed via an operational logic circuit 19, to an amplitude comparator 20 which compares the amplitude of the signal with a pre-established threshold amplitude value. In addition, the output signal from the power amplifier 18 is fed, via an operational logic circuit 21, to a frequency meter and frequency comparator 22 which compares the frequency of the said signal with a pre-established threshold frequency value.

The two operational logic circuits 19 and 21 have the function of enabling comparison of the amplitude and the resonant frequency of the system with the respective threshold values only after a predetermined time, such as to ensure that the system is in a stable condition of resonance, thus avoiding the possibility of erroneous transitory interpretations due to the mechanical locking and releasing of the piece 11 under test.

The output signals from the amplitude comparator 20 and from the frequency comparator 22 are passed to an acceptance logic circuit 23. A display device 24 connected to the acceptance logic circuit 23 is arranged to provide an indication if the amplitude and the resonance frequency exceed the pre-established thresholds, indicating therefore that the piece 11 under test is acceptable. Failure of the display device 24 to provide such an indication will indicate that the piece under test is unacceptable and should be rejected.

In order to establish the threshold values of frequency and amplitude to be introduced into the comparators 20 and 22, the calibration circuit, illustrated diagrammatically in FIG. 2 is used.

For the purpose of calibration two reference pieces 9 and 9a are affixed to the ends of the cross-piece 5 of the T-shaped mounting element 4, the reference piece 9 being selected to have a degree of spheroidization greater than 90%, and the reference piece 9a being selected to have a degree of spheroidization reaching the limit of acceptability, for example 70%. Thereafter a test piece 11 is mounted on the cross piece 5 in the place of reference piece 9a, as shown in FIG. 1, for making the test.

The calibration circuit includes a variable frequency electromagnetic oscillator 25 which applies to the transducer 12 a sinusoidal signal of constant amplitude, through a power amplifier 26. The accelerometer 13 is connected, via an input amplifier 27, to an amplitude reader 28 and to a frequency meter 29, which measure respectively the relative amplitude of acceleration in dB and the resonance frequency of the entire system, these measurements constituting the thresholds for the comparators 20 and 22.

In practice the electronic circuits of FIGS. 1 and 2 may conveniently be combined into one single circuit, in view of the presence in the circuits of common elements, with a switching arrangement for selectively rendering the circuit suitable for testing pieces or for determining the appropriate threshold values each time the type of piece to be tested in the apparatus is changed.

We claim:

1. A method of testing the quality of cast iron pieces comprising the steps of mechanically coupling together in a mechanical oscillatory system a piece to be tested and a reference piece having the same form and geometry as the piece to be tested, oscillating the said system at resonance, obtaining signals representing the frequency and resonance amplitude of the oscillating system, and utilizing said signals to provide an indication of the quality of the piece to be tested by comparing said signals with the same signals obtained with two reference pieces having different degrees of acceptability, one of said reference pieces representing a lower limit of acceptability, and wherein the test piece is substituted for said one reference piece.

2. Apparatus for testing the quality of cast iron pieces, the apparatus comprising:
   a fixed support structure;
   a cantilever support extending cantilever fashion from the said support structure;
   first fixing means for fixing a reference piece to the said support having a high degree of acceptability;
   second fixing means for fixing a piece to be tested to the said support;
   a transducer adapted to be attached to the said reference piece and to excite, in use of the apparatus, oscillation of the mechanical system consisting of the support, the reference piece and the piece under test;
   accelerometer means adapted to be applied to the said reference or datum piece for measuring the vibrations of said mechanical system in use of the apparatus, and
   an electronic circuit connected to said transducer and to said accelerometer means, said circuit including means for effecting resonant oscillations of the said mechanical system, means for measuring the amplitude and frequency of said resonant oscillations, comparator means for comparing said measurements with pre-established threshold values representing values obtained with reference pieces of high and low degrees of acceptability and wherein said reference piece of low degree of acceptability has been substituted by said test piece in said comparison and means for displaying the comparison provided by said comparator means.

3. The apparatus defined in claim 2, wherein the cantilever support comprises a T-shaped mounting element having a vertical cross-piece and a stem with an end remote from the cross-piece which is fixed to the support structure, the cross-piece being provided at its ends with the respective first and second fixing means for attachment of the reference or datum piece and the piece to be tested respectively.

4. Apparatus according to claim 2 or wherein the electronic circuit includes an accelerometer signal amplifier for signals provided by the accelerometer means, filter means which pass only these components at substantially the resonance frequency of the mechanical system, a power amplifier having an input connected to the filter means and an output connected to the transducer, and an amplifier comparator and frequency comparator connected respectively to the outputs of the accelereometer signal amplifier and of the power amplifier.

5. The apparatus defined in claim 4, including a squarer and a frequency divider interposed between the output of the accelerometer signal amplifier and the input of the filter means.

* * * * *